United States Patent [19]

Solano

[11] Patent Number: 5,056,533

[45] Date of Patent: Oct. 15, 1991

[54] SUPPORT CUSHION

[76] Inventor: Toni Solano, 113 Gayle St., Fort Morgan, Colo. 80701

[21] Appl. No.: 599,126

[22] Filed: Oct. 17, 1990

[51] Int. Cl.[5] ........................ A61G 15/00; A61G 7/08; A61F 5/37

[52] U.S. Cl. .................................... 128/845; 128/876; 5/81 R; 5/81 C

[58] Field of Search ............... 128/845, 870, 869, 875, 128/876, 877; 5/82 R, 81 R, 89, 83, 81 C

[56] References Cited

U.S. PATENT DOCUMENTS

| | | | |
|---|---|---|---|
| 1,035,642 | 8/1912 | Rosse | 5/89 |
| 1,538,538 | 5/1925 | Wood | 297/453 |
| 1,934,615 | 11/1933 | Selverstone et al. | 155/182 |
| 2,652,183 | 9/1953 | Hlivka | 227/49 |
| 2,782,839 | 2/1957 | Cole | 155/182 |
| 2,797,743 | 7/1957 | Rodtz, Jr. | 155/182 |
| 3,234,568 | 2/1966 | Fischer | 5/89 |
| 3,253,861 | 5/1966 | Howard | 297/453 |
| 4,124,908 | 11/1978 | Burns | 5/82 R |
| 4,478,453 | 10/1984 | Schutz | 297/219 |
| 4,568,125 | 2/1986 | Sckoinik | 297/467 |
| 4,665,908 | 5/1987 | Calkin | 5/82 R |
| 4,675,925 | 6/1987 | Littleton | 5/81 R |
| 4,695,092 | 9/1987 | Hittie | 297/230 |
| 4,739,526 | 4/1988 | Hollick | 5/83 |
| 4,742,588 | 5/1988 | James | 5/83 |
| 4,748,701 | 6/1988 | Marlowe | 5/89 |
| 4,761,032 | 8/1988 | Sanchez et al. | 297/229 |
| 4,824,168 | 4/1989 | Makoski | 297/229 |
| 4,862,904 | 9/1989 | West | 128/877 |
| 4,939,803 | 7/1990 | Waters | 5/82 R |
| 4,979,520 | 12/1990 | Boone, Jr. | 5/82 R |

*Primary Examiner*—Robert A. Hafer
*Assistant Examiner*—Michael Brown
*Attorney, Agent, or Firm*—Leydig, Voit & Mayer

[57] ABSTRACT

A flexible padded support cushion adapted for use with a chair or bed, especially a wheelchair. The cushion includes a back portion having a circumferential pad attached about its periphery to provide support for a patient's head. A seat portion is flexibly connected to the back portion and lifting handles are attached to the back and seat portions for aiding in transportation of the patient or the cushion. To increase comfort detachable pads are strategically arranged on both the back and the seat portions of the support cushion. The cushion may also be used with an automobile seat as a travel booster for children.

18 Claims, 2 Drawing Sheets

SUPPORT CUSHION

TECHNICAL FIELD

This invention relates generally to a padded support cushion which is used to provide maximum comfort, positional stability and support to elderly or handicapped individuals.

BACKGROUND OF THE INVENTION

Physically disabled patients must often be moved from one location to another. Frequently, this involves carrying a patient from a wheelchair to a bed, or vice versa. This can be a painful experience for the patient since he or she must be tightly clutched. Additionally, such carrying is usually a cumbersome and awkward task for caretakers of the patient.

Physical disabilities such as muscular dystrophy and arthritis frequently result in the patient experiencing acute atrophy of the muscles and severe inflammation of the joints. Weak hips are an equally hazardous disability for patients confined to wheelchairs as they are prone to slide into the armrest portion of a wheelchair causing the patient extreme discomfort. These conditions are not only painful but dangerous, especially during transport.

Existing support cushions have not been adequately adapted to remedy these discomforts suffered by the handicapped or the elderly.

Young children also suffer from discomfort and restlessness when travelling by car for long distances. It is widely recognized that booster seats can be used to improve safety and maximize a child's comfort. Typical booster seats, however, do not provide any head support so that when the child falls asleep its head slides off of the booster while its body is held substantially erect against the seat back due to the seat belt and shoulder harness. If the child is holding food or drink when it falls asleep, the driver must protect against spills thereby disturbing the driver's concentration —a situation that can make driving potentially hazardous.

SUMMARY OF THE INVENTION

The support cushion which is the subject of the present invention may be configured for use with any type of seat, bed, or chair including use as a child safety travel booster in an automobile. In the above-mentioned instances, the cushions provide added support and comfort to the user. Should the user be disabled, the cushion can be used to conveniently transport him with minimum discomfort.

The principal object of this invention is to provide a novel support cushion for individuals confined to a bed or wheelchair.

Another object of this invention is to provide an improved means for comfortably transporting individuals who are confined to beds or wheelchairs.

Yet another object of this invention is to provide a support cushion having pockets and intravenous (IV) tube supports to readily accommodate disabled users.

Still another object of this invention is to provide a novel support cushion for use with a child safety travel booster in an automobile.

These and other objects are satisfied by a support cushion comprising:

a generally flexible unitary body piece defined by a casing having back and seat portions encompassing a cushion insert;

lifting handles attached to a side edge of the back and seat portions respectively for aiding in transport of a patient or the cushion; and an elliptical circumferential pad attached to the casing at the periphery of the back portion for supporting the patient's head.

Hereinafter "patient" will be used to describe a physically incapacitated user of the cushion and "caretaker" will be used to describe the person or persons involved with care and transport of the patient.

DESCRIPTION OF THE ILLUSTRATED EMBODIMENT

Figure 1:
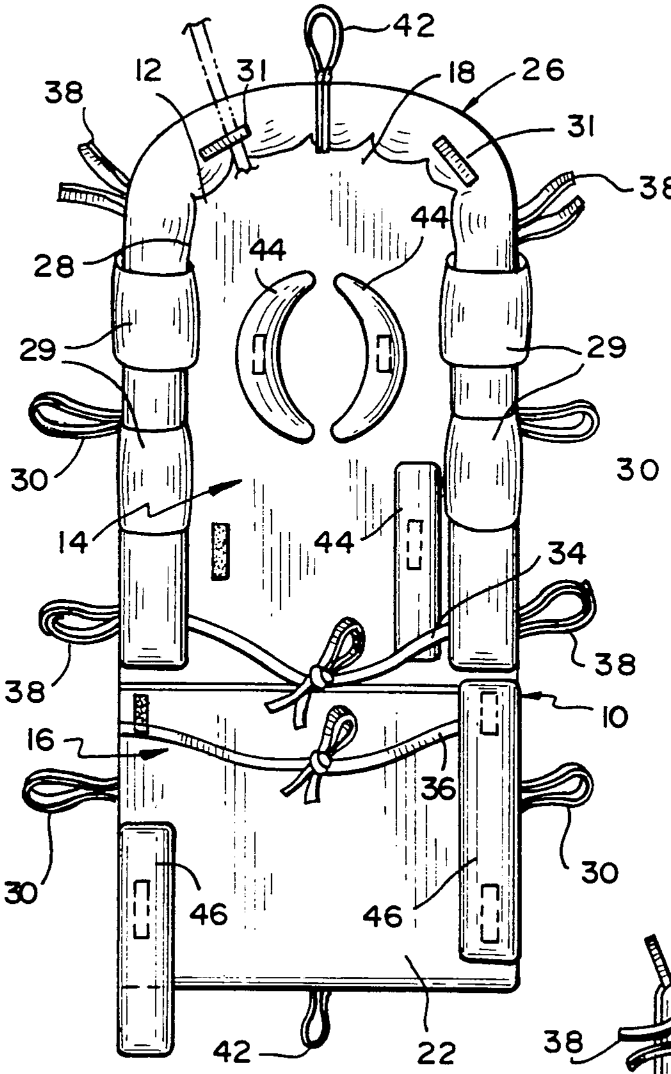
FIG. 1 is a front view of a support cushion of this invention in a fully extended condition.

An embodiment of the present invention is depicted in FIG. 1 illustrating a support cushion comprising a body piece 10 defined by a casing 12 having a back portion 14 and a seat portion 16 and encompassing a cushion insert (not illustrated). Back portion 14 has a front surface 18 and a rear surface 20. Seat portion 16 has a front surface 22 and a rear surface 24.

In the illustrated embodiment, casing 12 is constructed of a unitary sheet of heavy gauge canvas overlying a cushion insert constructed from foam padding. Accordingly, body piece 10 is flexible so that back portion 14 can be inclined and reclined relative to the bed, chair or other supporting structure with which it is used. In FIGS. 1–4 the sheet is stitched together to form a permanent casing for the cushion insert. However, to make cleaning easier, the sheet can be secured using a zipper, snap fasteners or a Velcro® closure, thus allowing the cushion insert to be readily removed from the casing and allowing both the insert and the casing to be easily cleaned and replaced.

Figure 2:
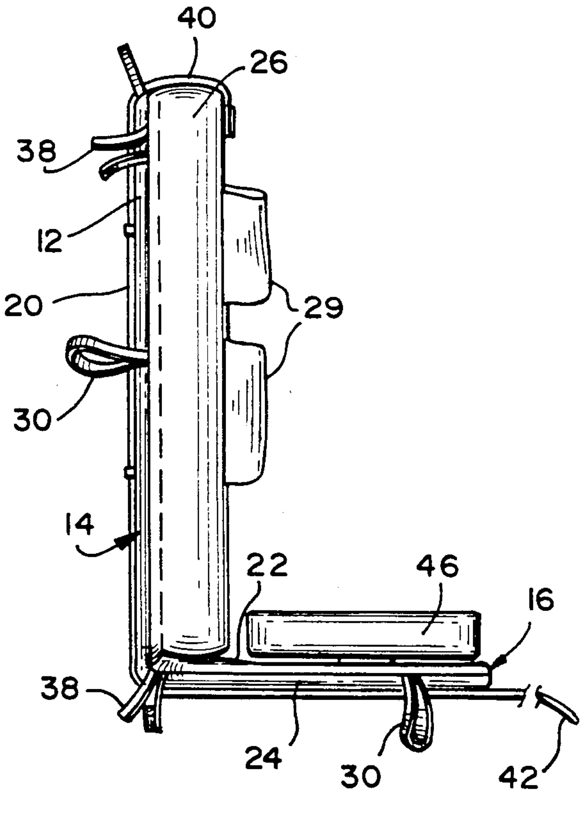
FIG. 2 is a side view of the support cushion with the back portion in an erect condition.

Head and upper body support for the patient is provided by elliptical circumferential pad 26 depicted in FIG. 2 attached along the periphery to the front surface of back portion 14. Similar to body piece 10, the elliptical circumferential pad comprises a foam cushion insert enveloped by a heavy gauge canvas covering 28. Circumferential support pad covering 28 can be attached to back portion 14 by stitching, etc. or it can be fashioned from the same sheet of canvas comprising body piece casing 12 as for example, by rolling the top and side edges of the back portion 14 over a cushion insert and securing them on the front surface of back portion 14.

Pockets 29 are stitched to circumferential support pad covering 28 at selected locations. In the illustrated embodiment there are two pockets disposed on one side of circumferential support pad covering 28 adjacent the arms of the patient. Symmetrical counterparts are disposed on the opposite side. The patient can minimize reliance on the caretaker by utilizing the pockets to carry books, liquid beverage containers, medication or other items which the caretaker would otherwise have to supply. Of course, the number of pockets and their positioning can be altered to suit the requirements of a particular patient.

Tube support members 31, comprised of Velcro® strips, are attached to circumferential pad covering 28 immediately above pockets 29. A patient who is using an IV device can position the IV tube in the tube support member 31 and thereby secure the IV tube in the most convenient position. In addition pockets 29 cooperate with tube support members 31 to form a beverage container holder. A canned or bottled beverage can be secured in a pocket while tube support member 31 secures a straw in a position allowing the patient to consume the drink without further adjustment.

The elliptical circumferential support pad 26, when attached to the back portion 14 acts as a barrier to resist movement of the patient relative to the support cushion. Chest belt 34 and lap belt 36 are additional features incorporated with body piece 10 to positionally stabilize and restrict lateral movement of the patient. Each belt consists of two strips of canvas, each being attached to an opposing side edge of body piece 10. The two strips extend substantially across the width of the body piece and can be fastened using a slip knot or any appropriate clamping device. As depicted in FIG. 1, chest belt 34 is attached to the lower sector of back portion 14 while lap belt 36 is attached to the upper sector of seat portion 16. The relative location and number of belts may be varied according to the patient's particular needs.

When transporting a patient, it is desirable and commonly necessary to prevent discomfort caused by the patient being jostled relative to the cushion support. Accordingly, as illustrated, lifting handles 30 are attached to the side edges of back portion 14 and seat portion 16, respectively. Lifting handles 30 are made of heavy gauge canvas arranged in a loop and are positioned approximately at the midpoint of the side edges of back portion 14 and seat portion 16. More particularly, the lifting handles are symmetrically arranged in pairs with each pair member having its counterpart at an opposing edge of body piece 10. For example, the lifting handle attached to a side edge of seat portion 16 has a symmetrically aligned counterpart attached to the opposing edge. Likewise, the handle attached to a side edge of back portion 14 has a symmetrically aligned counterpart attached to the opposing edge to provide stability for the patient and the caretaker during transport. Each lifting handle is interconnected via reinforcing support straps 32 stitched to the rear surface of body piece 10. Each support strap 32 is comprised of a strip of canvas which extends across the width of body piece 10. The lifting handles are established by looping the ends of the support straps 32 and stitching them together. As the caretaker transports the patient, support straps 32 act as reinforcing ribbing to aid in preventing the support cushion from sagging, an acute concern when dealing with infirm patients.

Figure 3:
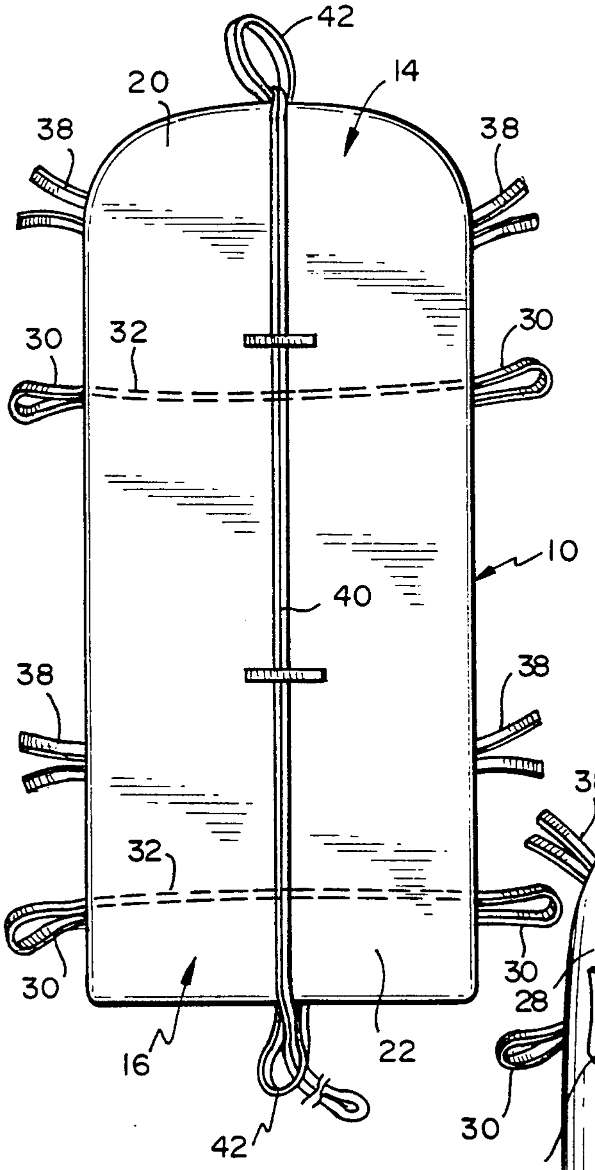
FIG. 3 is a rear view of the support cushion.

Referring now to FIG. 3, securing straps 38 and tie down rope 40 are shown connected along the side and top edges of body piece 10, respectively, for securing the support cushion to a desired structure such as a bed or wheelchair. Tie down rope 40 is stitched to the top edge of the front surface of back portion 14 immediately below elliptical circumferential pad 26. The rope traverses body piece 10 lengthwise and extends past the bottom edge of seat portion 16. A tie down rope loop 42 is attached to the bottom edge of seat portion 16. When using the support cushion with a chair, the caretaker can draw the tie down rope over the back of the chair and guide it underneath the seat where it can be fastened to the tie down rope loop 42 thereby securing the support cushion to the chair. In addition to securing straps 38 and tie down rope 40, body piece 10 can be provided with slots to accommodate those supporting structures already equipped with straps, belts and the like.

Figure 4:
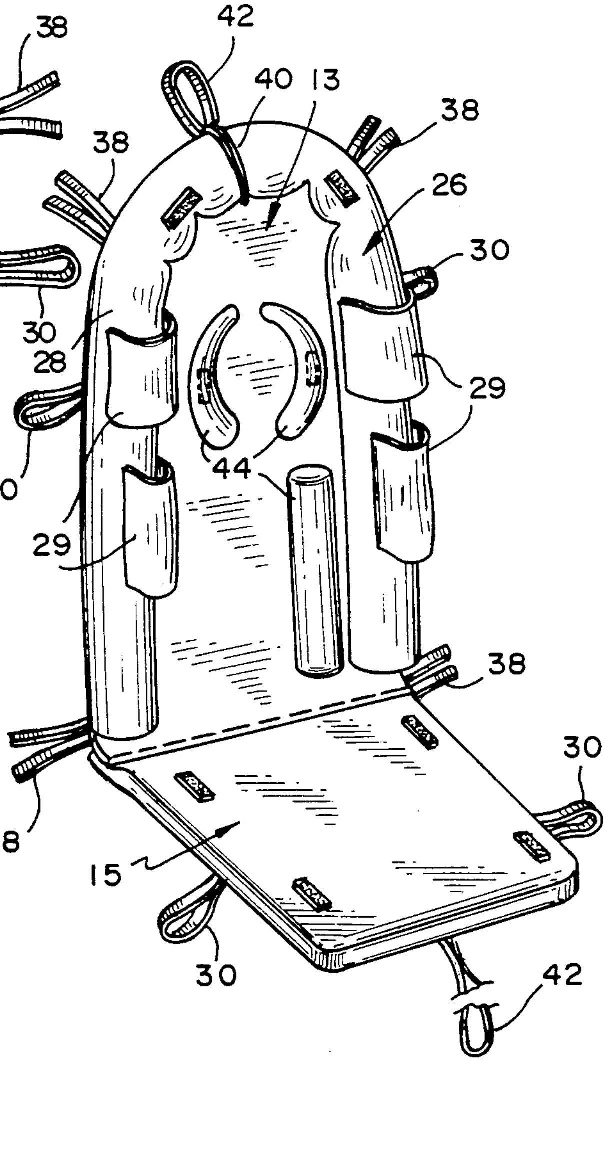
FIG. 4 is a front view of the support cushion with the back portion in an erect condition.

The body piece 10 is also equipped with detachable support pads 44 and lap cushions 46 each comprising an outer covering of heavy gauge canvas encompassing a cushion insert as seen in FIGS. 1,2 and 4. Body piece 10 and the detachable pads 44 are both fitted with Velcro® fasteners so that the detachable pads can be connected to the body piece in an arrangement that would be most accommodating to a particular patient. Detachable support pads 44 and lap cushions 46 provide for customizing the cushion, not only to render additional stability but also to enable modification to maximize the patient's comfort. Consequently, in order to match the contours of a patient's body, support pads 44 and lap cushions 46 are configured in a variety of shapes including crescents, cylinders, spheres, and the like. For instance, a crescent shaped detachable support pad 44 is attached to the front surface of back portion 14 at either side of the patient's head. Such a configuration is particularly helpful to a patient having weak neck muscles as it cradles the head and provides additional support, thus restricting undesired movement of the head.

FIG. 4 illustrates a modification of the support cushion where body piece casing 12 is divided into back section 13 and seat section 15. Accordingly, each section comprises a separate casing encompassing its own associated cushion insert. Back section 13 and seat section 15 can be stitched together so that there is a canvas barrier hingedly connecting back section 13 and seat section 15.

It should be noted that the application of the support cushion is not limited to the environments discussed heretofore. For example, in smaller sizes it can be used in an automobile as a travel cushion for a child's booster seat or a seat cushion for a high chair. The advantages of the pockets for storing diapers, bottles, etc., should be evident. The body piece can also aid emergency rescue and ambulance personnel in the transport of patients. Furthermore, although the above-mentioned cushion inserts are comprised of foam, an inflatable plastic bladder, fiberfill or other like structures may be employed, making storage easy and convenient. For example, support pad 26, detachable pads 44 and lap cushions 46 may be inflatable and attached to body piece 10 as described.

In view of the foregoing description it should be apparent that the support cushion is adaptable to extensive variation and modification and suitable for a variety of uses. Accordingly, it is appreciated that the skilled artisan, in light of the above teachings, may so modify the invention without departing from the scope and spirit of the appended claims.

The inventor claims:

1. A support cushion comprising:

a generally flexible unitary body piece defined by a casing having back and seat portions encompassing a cushion insert;

lifting handles attached to a side edge of the back and seat portions respectively for aiding in transport of a patient or the cushion;

an elliptical circumferential pad attached to the casing at the periphery of the back portion for supporting the patient's head; and said circumferential pad includes a plurality of pockets for storage.

2. A support cushion according to claim 1, wherein said circumferential pad includes at least one tube support member for supporting an IV tube.

3. A support cushion according to claim 1, wherein said lifting handles are attached generally at a midpoint of each side edge of the back and seat portions respectively for aiding in transport of a patient or the body piece.

4. A support cushion according to claim 1, further comprising a plurality of belts connected to the back and seat portions extending from one side edge to the other for securing the patient to the cushion.

5. A support cushion according to claim 1, further comprising a plurality of detachable pads attached to the back and seat portions respectively.

6. A support cushion according to claim 1, wherein said casing is replaceable.

7. A support cushion according to claim 1, further comprising a tie down rope attached to the top edge of the back portion, traversing the body piece lengthwise, and extending past the bottom edge the seat portion, for securing the cushion to a chair.

8. A support cushion according to claim 5, further comprising lap cushions attached to said seat portion.

9. A support cushion comprising:

a generally flexible unitary body piece defined by a casing encompassing a cushioned insert including a back portion having front and rear surfaces and a seat portion having front and rear surfaces;

lifting handles attached to each side edge of the back and seat portions respectively for aiding in transport of a patient or the body piece;

an elliptical circumferential pad attached to the casing at the periphery of the front surface of the back portion for supporting the patient's head;

securing straps attached along the periphery of the rear surface of the back and seat portions for securing the cushion to a supporting structure; and a plurality of belts connected to the back and seat portions extending from one side edge to the other for securing the patient to the cushion.

10. A support cushion according to claim 9, wherein said lifting handles are interconnected by support straps extending across the back and seat sections respectively from one side edge to the other.

11. A support cushion according to claim 9, further comprising a plurality of detachable pads attached to the back and seat portion respectively.

12. A support according to claim 10, wherein the casing is composed of canvas.

13. A support cushion according to claim 9, wherein said lifting handles are defined by a looped strip of canvas.

14. A support cushion comprising:

a sectioned body piece having a back section hingedly connected to a seat section, said seat and back sections each having a cushion insert;

an elliptical circumferential pad attached to the back section along the perimeter for supporting the patient's head;

lifting handles attached generally at a midpoint of each side edge of the back and seat sections respectively, interconnected by support straps extending across the back and seat sections respectively from one side edge to the other, for providing aid in transport of patients.

15. A support cushion according to claim 14, including a plurality of detachable support pads attached to the back and seat portions respectively.

16. A support cushion according to claim 14, including a tie down rope attached to the top edge of the back portion, traversing the body piece lengthwise, and extending past the bottom edge of the seat portion, for securing the cushion to an automobile seat.

17. A support cushion according to claim 14, including a beverage container holder attached to said circumferential pad.

18. A support cushion according to claim 17, wherein said beverage container holder is defined by a pocket positioned immediately below a tube support member so that the patient can easily drink beverages from a straw.

* * * * *